United States Patent
Bodenschatz et al.

(10) Patent No.: US 6,447,470 B2
(45) Date of Patent: *Sep. 10, 2002

(54) SELF-ADHESIVE READY-TO-USE BANDAGE FOR LIGAMENT AND MUSCLE STABILIZATION AT THE KNEE JOINT

(75) Inventors: Stefan Bodenschatz; Peter Himmelsbach, both of Buxtehude (DE)

(73) Assignee: Beiersdorf AG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/966,127

(22) Filed: Nov. 7, 1997

(30) Foreign Application Priority Data

Nov. 13, 1996 (DE) .......................................... 196 46 740

(51) Int. Cl.[7] ............................. A61F 5/00; A61F 13/00; A61F 15/00
(52) U.S. Cl. ............................. 602/75; 602/41; 602/62
(58) Field of Search .................... 602/1, 26, 60–63, 602/75–77, 79, 903, 41–59, 64–66, 20, 23; 606/180; 128/881, 882, 888, 889, 892

(56) References Cited

U.S. PATENT DOCUMENTS

| | | | | |
|---|---|---|---|---|
| 3,046,981 A | * | 7/1962 | Biggs, Jr. et al. | 602/26 |
| 3,138,158 A | * | 6/1964 | Gordan et al. | 604/180 |
| 3,853,598 A | * | 12/1974 | Raguse | 602/903 X |
| 4,423,720 A | * | 1/1984 | Meier | 602/26 |
| 4,734,320 A | * | 3/1988 | Ohira et al. | 602/75 X |
| 5,538,500 A | * | 7/1996 | Peterson | 602/20 X |
| 5,711,312 A | * | 1/1998 | Staudinger | 602/23 X |
| 5,792,091 A | * | 8/1998 | Staudinger | 602/20 X |

FOREIGN PATENT DOCUMENTS

| | | | | |
|---|---|---|---|---|
| DE | 19646740 | * | 5/1998 | 602/26 |
| WO | 94000082 | * | 1/1994 | 602/26 |

* cited by examiner

*Primary Examiner*—Denise Pothier
(74) *Attorney, Agent, or Firm*—Norris McLaughlin & Marcus

(57) ABSTRACT

Ready-to-use bandage self-adhesively coated on one side, for relieving, stabilizing and functionally restricting the ligament and muscle structures of the knee joint, comprising a substantially rectangular central part (A) which is at least partially inelastic in the transverse direction of the bandage and on which there are respectively arranged, directed upwards and downwards seen in the longitudinal direction, two elongate strips (B, C, D and E).

3 Claims, 2 Drawing Sheets

SELF-ADHESIVE READY-TO-USE BANDAGE FOR LIGAMENT AND MUSCLE STABILIZATION AT THE KNEE JOINT

The invention relates to a ready-to-use bandage which has a self-adhesive coating on one side and which is used for supporting and stabilizing the lateral ligament of the knee joint (Lig. collaterale fibulare). The resultant relief of the outer lateral ligament is used in particular for the treatment of lateral instability caused by atrophic musculature, contusions, sprains, overstraining or slight tearing of the lateral ligaments. Furthermore, the bandage may be used as a relieving bandage for other indications, in particular for relief of the ischiocrural musculature.

BACKGROUND OF THE INVENTION

The functional bandaging technique, so-called taping, is a common treatment method for the prevention and therapy of injuries, disorders and changes of the locomotor system. The aim of taping is to simulate specifically the individual soft parts and capsular ligament structures and selectively support their functions.

The tape bandage, which is preferably made of inelastic material, although sometimes combined with elastic material, is applied in the form of several bands, so-called straps, in strip formation, and then performs the functions of supporting and relieving.

However, bandages of this type require special ability and a great deal of experience to apply and therefore cannot generally be applied by someone inexperienced in taping.

The object of the invention was therefore to make available a ready-to-use bandage which, by virtue of its configuration, i.e. design and shape, and also the properties of the material, results in the relief, fixing, stabilization and/or functional restriction of the ligament and muscle structures of the knee joint, in particular of the lateral ligament, and can be applied by the user in a simple way, if need be by himself.

BRIEF SUMMARY OF THE INVENTION

This object is achieved by a ready-to-use bandage self-adhesively coated on one side, for relieving and stabilizing ligament and muscle structures at the knee joint, comprising a substantially rectangular central part A which is at least partially inelastic in the transverse direction of the bandage and on which there are respectively arranged, directed upwards and downwards seen in the longitudinal direction, two elongate strips B, C, D and E, said bandage being sized and configured to be applied to a generally outstretched leg.

The central part A is preferably of an inelastic design, seen in the transverse direction of the bandage, but may also be only partially inelastic, for example in such a way that the material is elastic or extensible in this direction, but has inelastic reinforcing strips. In the applied state, the part A is intended to run substantially in the longitudinal direction of the leg, as will be shown later. is thus the effective direction of this part of the bandage.

The central part A has as a whole, or at least partially, a maximum elongation under tensile force of less than 30% in the transverse direction of the bandage.

The strips B, C, D and E may be arranged on the part A at an angle $\alpha$ of from 30 to 150°, with respect to the transverse direction of the bandage, all variations in the alignment of the respective strips being possible. They are, however, preferably perpendicularly disposed on the central part A, i.e. the angle $\alpha$ is 90° and the four long strips run parallel to one another.

The length of the strips is predetermined by their application technique, which is described more precisely further below. By way of example, the length of the bandage is altogether about 70–110 cm, preferably 100 cm, and it is about 2–16 cm, preferably 10 cm, wide. At the same time, the central part A is about 10 cm long and about 2–16 cm, preferably 10 cm, wide and the strips B, C, D and E are about 30–50 cm, preferably 45 cm, long and about 1–8 cm, preferably 5 cm, wide. Depending on the relative size of the joint to be bandaged, they may also be longer and wider or, if appropriate, be shortened. Furthermore, the strips (straps) may be differently designed, for example they may vary in thickness, width, length textile-related technical data, but also may be partially divided.

DETAILED DESCRIPTION

The bandage is designed altogether in one piece, it either being cut out or punched out as a whole from a larger piece of bandage material or being joined together from individual parts.

It is particularly preferred for it to consist of a textile material which is extensible or elastic in one direction, preferably of a woven or nonwoven fabric which is extensible or elastic in one direction, in particular on a cotton base, having a maximum tensile strength of preferably at least 60 N/cm and an elongation under loading of 10 N/cm of up to about 90%, preferably 10% to 80%, in the longitudinal direction. In the other direction, the maximum elongation under tensile force is at most 30%. The material is aligned in the bandage such that the central part A is at least partially inelastic in the transverse direction.

The central part A is to be at least partially inelastic in the transverse direction, so that when the bandage is produced from the said basic material it is elastic in the longitudinal direction and inelastic in the transverse direction.

It has proven particularly favourable if a small clearance is located at the inner incision between the strips B/C and D/E, in order to prevent tearing and to make fixing easier.

On its side facing the skin, the bandage is coated with one of the known readily adhering self-adhesive compositions based on rubber or synthetic polymers. This should preferably be air-permeable and water-vapour-permeable and should have good skin compatibility.

Until the bandage is used, the adhesive layer may be covered with a sheet material treated so as to be adhesive-repellent, for example siliconized paper or plastic film.

It has proven favourable in this case to design this covering in several parts, preferably in 5 parts, by means of, for example, perforated separating lines. In this case, one part covers the central part A and 4 further strip-shaped parts cover the narrower strips B, C, D and E. As an aid to application, the covering parts may be colour-marked or numbered.

When applying the bandage to the outstretched or slightly bent (<30°) knee joint, the central part A is firstly fixed on the outer side of the knee joint. This takes place in such a way that it is adhesively fixed widthwise—that is to say in the transverse direction—distally from the upper leg attachment to the lower leg attachment. The strips B, C, D, E, which are technically referred to as straps, form a 90° angle with respect to the leg. Then, the strip B is led on the rear side in a circular motion from lateral to medial on the upper leg and adhesively fixed in place, so that it encloses at least part of, preferably the entire upper leg at least once. As the next strap, the strip C is applied. This likewise runs on the rear side in a circular motion from lateral to medial on the lower leg. This strap is likewise to enclose part of, preferably the entire lower leg at least once. In the case of both the straps B and C, it must be ensured that the region of the hollow of the knee is not adhesively covered.

The strap D is applied such that it runs on the front side distally to the lower leg and is adhesively fixed there in a circular motion from medial to lateral. The strap is to enclose at least part of, preferably the entire lower leg at least once.

Finally the strap E is applied. It is led proximally from the lower leg to the upper leg and there in a circular motion coming from medial to lateral.

The adhesive-repellent covering materials on the strips are successively removed in a way corresponding to the procedure when they are adhesively fixed. The bandage may additionally be strengthened by anchoring strips of customary tape material.

Once applied, the bandage supports, fixes, stabilizes and relieves the ligament and muscle structures of the knee joint, in particular of the lateral ligament, the stabilization of the joint being ensured by the strip A, which is inelastic in the transverse direction, the strips B, C, D and E acting in a fixing and supporting way.

Simplified application of the ready-to-use bandage is also possible, however. In this case, the straps D and E are led only in a circular motion around the lower or upper leg. By overlapping the straps B/D and C/E, fixing of the central part A is ensured even under severe loading. In this case, the straps B and C can additionally be led under the central part A. This strengthens the fixing.

If the bandage is used for other muscle or ligament structures, it is to be applied such that the orientation of the transverse direction of the central part A runs in a way corresponding to the structure to be supported. For example, the hollow of the knee is the starting point for a relieving bandage for the ischiocrural musculature. The application of the straps B, C, D and E of the ready-to-use bandage is to be carried out in a way analogous to the simplified application described above, in that they are led in a circular motion around the lower or upper leg.

BRIEF DESCRIPTION OF THE DRAWINGS

The bandage according to the invention is represented by way of example in

Figure 1:
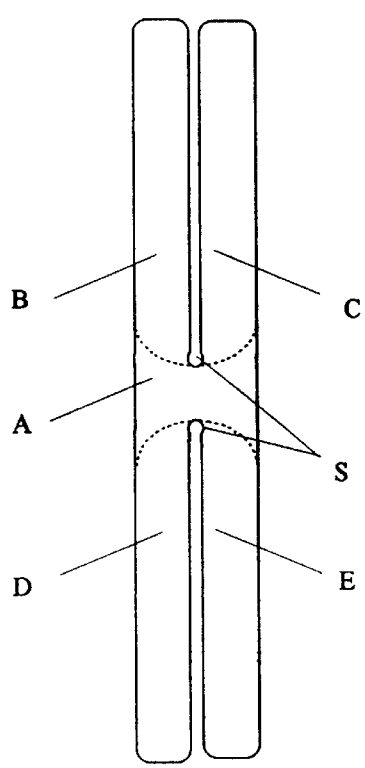
FIG. 1, the elongate strips (straps) B, C, D and E being arranged perpendicularly with respect to the central part A, i.e. the angle α is 90°. S denotes the point of intersection of A, B and C or A, D and E. The dashed lines indicate the perforation in the covering on the adhesive side of the bandage.
Figure 2:
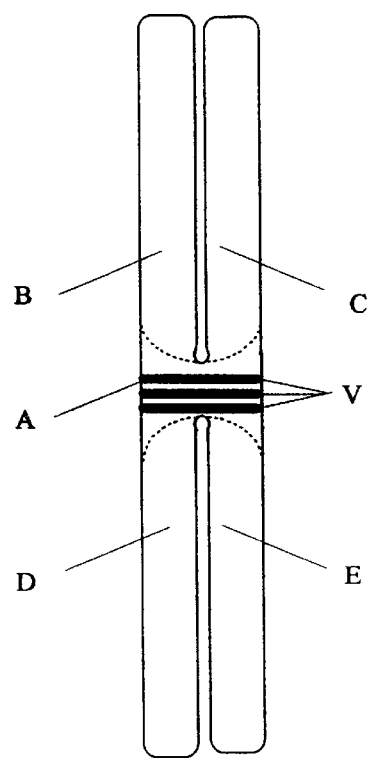
FIG. 2 shows by way of example a longitudinally and transversely elastic bandage having three inelastic reinforcing strips (V), which are joined, to the bandage in the transverse direction in the central part A. As a result, the central part A is partially inelastic in the transverse direction and consequently effective in the way according to the invention.
Figure 3:
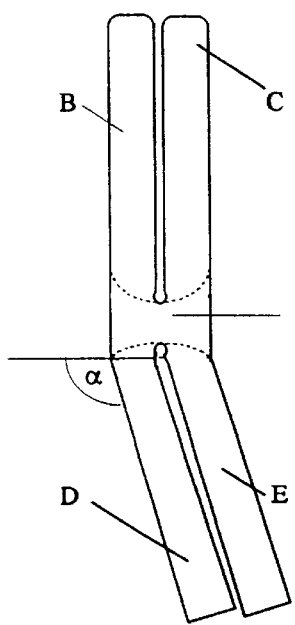
FIGS. 3–5 show under a, b and c three variations of the arrangement of the straps B, C, D and E with an angle α of the straps D and E with respect to the transverse direction of the bandage of in each case about 115° at a and in each case about 65° at b as well as about 65° for D and about 115° for E at c.
Figure 4:
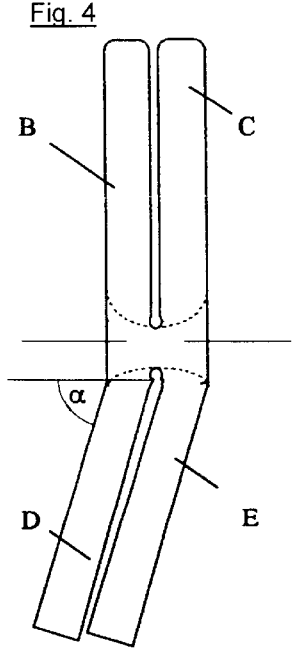
Figure 5:
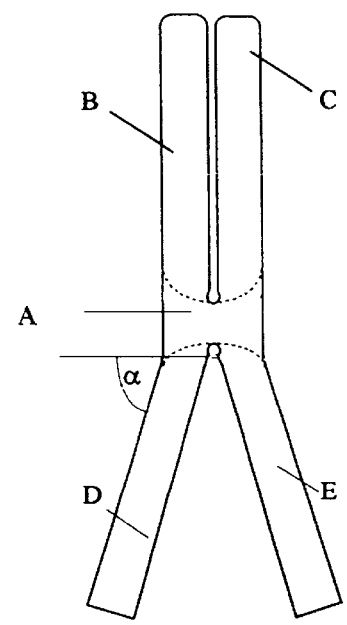
Figure 6:
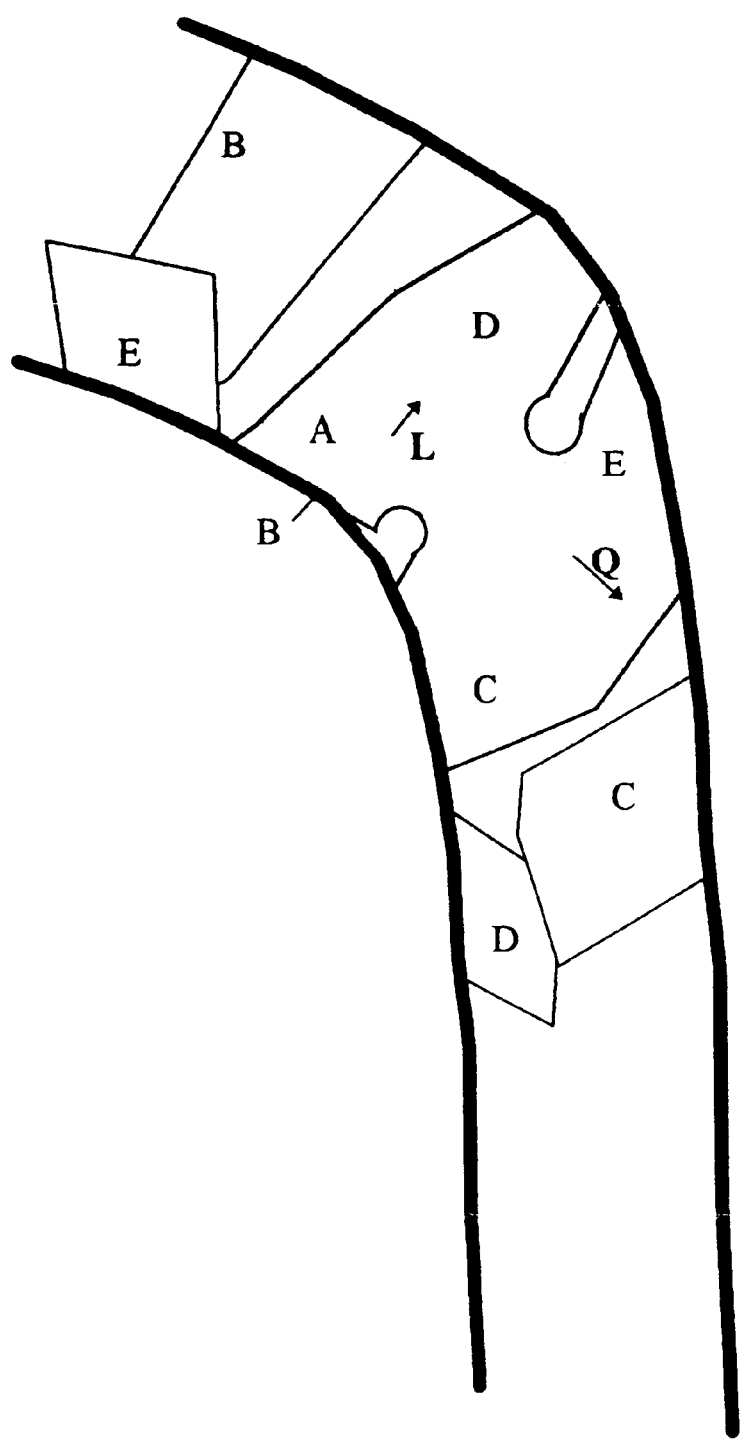
FIG. 6 shows the bandage in the applied state, wrapped around in the way described further above.

We claim:

1. A method for relieving, fixing and stabilizing the outer lateral ligament of the knee joint, which comprises applying to an outstretched leg a self-adhesive bandage for relieving and stabilizing the lateral ligament of the knee joint, comprising an adhesive on a first side of the bandage, a substantially rectangular central part, the central part being about 10 cm long and about 2 to 16 cm wide and having a maximum elongation under tensile force of less than 30% in the transverse direction and having first and second longitudinal ends and four elongate strips, each of which is of a length sized and configured to encircle the leg of a patient at least once, a first pair of said elongate strips being adjacent the first longitudinal end of the central part and a second pair of said elongate strips being adjacent the second longitudinal end of the central part, said bandage being sized and configured to be applied to a generally outstretched leg and arranging said bandage so that the central part is aligned in its transverse direction over the outer lateral ligament of the knee and each of said strips is wrapped around the leg either above the knee or below the knee, and each of said strips encircles the leg at least once.

2. Method according to claim 1, wherein one strip of the first pair of strips is wrapped around the rear side of the upper leg in a circular motion from lateral to medial, the second strip of said first pair is wrapped around the rear side of the lower leg in a circular motion from lateral to medial, one strip of the second pair of strips is wrapped around the front side of the leg distally to the lower leg and from there in a circular motion from medial to lateral and the other strip of said second pair is wrapped around the front side of the leg proximally from the lower leg to the upper leg and from there in a circular motion from medial to lateral.

3. A method for relieving, fixing and stabilizing the outer lateral ligament of the knee joint, which comprises applying to an outstretched leg a self-adhesive bandage for relieving and stabilizing the lateral ligament of the knee joint, comprising an adhesive on a first side of the bandage, a substantially rectangular central part, the central part being about 10 cm long and about 2 to 16 cm wide and having a maximum elongation under tensile force of less than 30% in the transverse direction and having first and second longitudinal ends and four elongate strips, each of which is of a length sized and configured to encircle the leg of a patient at least once, a first pair of said elongate strips being adjacent the first longitudinal end of the central part and a second pair of said elongate strips being adjacent the second longitudinal end of the central part, said bandage being sized and configured to be applied to a generally outstretched leg and arranging said bandage so that the central part is fixed in the hollow of the knee and each of said strips is wrapped around the leg either above the knee or below the knee, and each of said strips encircles the leg at least once.

* * * * *